United States Patent
Fabregas Vidal et al.

(10) Patent No.: US 10,413,568 B2
(45) Date of Patent: Sep. 17, 2019

(54) ORAL PHARMACEUTICAL COMPOSITION FOR DRUGS WITH A HIGH-DOSAGE REGIMEN

(71) Applicant: LABORATORIOS RUBIO, S.A., Castellbisbal (ES)

(72) Inventors: Jose Luis Fabregas Vidal, Barcelona (ES); Nuria Ruiz Xiville, Badalona (ES)

(73) Assignee: LABORATORIOS RUBIO, S.A, Castellbisbal (ES)

( * ) Notice: Subject to any disclaimer, the term of this patent is extended or adjusted under 35 U.S.C. 154(b) by 0 days.

(21) Appl. No.: 14/651,931

(22) PCT Filed: Dec. 5, 2013

(86) PCT No.: PCT/ES2013/070845
§ 371 (c)(1),
(2) Date: Jun. 12, 2015

(87) PCT Pub. No.: WO2014/096485
PCT Pub. Date: Jun. 26, 2014

(65) Prior Publication Data
US 2015/0306135 A1    Oct. 29, 2015

(30) Foreign Application Priority Data
Dec. 21, 2012 (ES) .................................. 201231993

(51) Int. Cl.
| | | |
|---|---|---|
| A61K 31/795 | (2006.01) |
| A61K 9/00 | (2006.01) |
| A61K 36/68 | (2006.01) |
| A61K 31/785 | (2006.01) |
| A61K 31/787 | (2006.01) |
| A61K 31/717 | (2006.01) |
| A61K 47/10 | (2017.01) |
| A61K 47/14 | (2017.01) |
| A61K 9/06 | (2006.01) |
| A61K 47/44 | (2017.01) |

(52) U.S. Cl.
CPC .......... *A61K 31/795* (2013.01); *A61K 9/0053* (2013.01); *A61K 9/0056* (2013.01); *A61K 9/06* (2013.01); *A61K 31/717* (2013.01); *A61K 31/785* (2013.01); *A61K 31/787* (2013.01); *A61K 36/68* (2013.01); *A61K 47/10* (2013.01); *A61K 47/14* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 4,221,778 A | 9/1980 | Raghunathan | |
| 4,882,152 A * | 11/1989 | Yang | A61K 9/0056 424/440 |
| 6,740,350 B2 * | 5/2004 | Pfeiffer | A23G 3/0205 426/572 |
| 2005/0009793 A1 * | 1/2005 | Curd | A61K 9/1075 514/167 |

FOREIGN PATENT DOCUMENTS

| | | |
|---|---|---|
| EP | 0347014 A1 | 12/1989 |
| EP | 0492235 A1 | 7/1992 |
| JP | 2001086956 A | 3/2001 |
| WO | 2004047673 A2 | 6/2004 |
| WO | 2011141028 A1 | 11/2011 |

OTHER PUBLICATIONS

International Search Report, International Application No. PCT/ES2013/070845, dated Mar. 17, 2014, 1 page.
Spanish Search Report, ES Application No. 201231993, dated Nov. 19, 2013, 1 page.

\* cited by examiner

*Primary Examiner* — Melissa L Fisher
(74) *Attorney, Agent, or Firm* — Rothwell, Figg, Ernst & Manbeck, P.C.

(57) ABSTRACT

The present invention relates to an oral pharmaceutical composition for drugs with a high dosage regimen, specifically, ion exchange resins and bulk-forming laxatives. Said composition comprises the combination of a liquid oily component and a texturizing agent, giving the composition good organoleptic properties that allow taking drugs with a high dosage regimen without the usual problems associated with their poor palatability. The invention also relates to a method for preparing said composition and to the use thereof for the treatment of various pathologies. Furthermore, the invention also relates to an adduct formed between a polyol and an ion exchange resin, to a method for preparing it, and to the use thereof to improve resin palatability.

17 Claims, No Drawings

ORAL PHARMACEUTICAL COMPOSITION FOR DRUGS WITH A HIGH-DOSAGE REGIMEN

CROSS-REFERENCE TO RELATED APPLICATIONS

The present application is a national stage filing under 35 U.S.C. § 371 of PCT/ES2013/070845, filed on 5 Dec. 2013, which is related to and claims priority to Spanish Patent Application No. P 201231993, filed 21 Dec. 2012. Each application is incorporated herein in its entirety.

TECHNICAL FIELD

The present invention belongs to the field of pharmaceutical compositions, and more specifically relates to an oral pharmaceutical composition that is suitable for the administration of certain active ingredients that must be taken in high doses to solve the problems of poor palatability.

PRIOR ART

There are specific drugs which must be taken in considerably high doses, comparatively much higher than those of most active ingredients, to be able to exert their therapeutic effect in a suitable manner.

Ion exchange resins and bulk-forming laxatives particularly stand out among such drugs with a high dosage regimen.

Said drugs generate a significant problem when preparing suitable dosage forms. The most common oral dosage forms, such as tablets or capsules, are generally unsatisfactory because they require taking multiple units to reach the effective dose, which is quite impractical and makes it hard to comply with the therapy, and for active ingredients which a higher dosage regimen, they are unacceptable.

These drugs are often administered in powder form or granules which usually have to be taken with water or other liquids, or with food. These dosage forms also have drawbacks, mainly because said drugs often have problems of poor palatability, derived from their gritty texture, and poor flavor.

Another drawback of powder or granule forms is that in practice they require taking significant amounts of water to help ingest all of the active ingredient. This is contraindicated for patients with specific pathologies, particularly for patients with kidney conditions, who usually suffer hyperkalemia and require treatment with polystyrene sulfonate resins.

A considerable number of formulations have been described in the state of the art in order to solve said drawbacks. Some of them are based on incorporating said active ingredients in solid compositions with a grain base, in the form of dietary supplements, such as cereal bars or cookies, as described, for example, in documents EP-A-0347014, U.S. Pat. No. 5,695,749 and EP-A-0492235 for cholestyramine compositions, or in documents EP-A-0309029 or EP-A-0387933 for *psyllium* compositions. However, such compositions can be difficult to prepare, do not adapt to all active ingredients, nor are they easily ingested by all patient groups.

Compositions with a soft, semisolid consistency incorporating active ingredients with a high dosage regimen have also been described, in which attempts are made to solve the poor palatability by combining them with food products with a pasty consistency, generally containing a high proportion of sugars, as described, for example, in U.S. Pat. No. 5,258,181, wherein *psyllium* fiber is combined with peanut paste, or in patent application WO-A-92/08367, where *psyllium* is combined with almond paste.

Alternatively, European patent application EP-A-1004310 describes formulations in the form of gel suitable for the administration of ion exchange resins such as calcium polystyrene sulfonate or cholestyramine, for example. Said compositions contain a high proportion of sugars, comprised between 30% and 50% by weight with respect to the total weight of the components except water. Said gelled compositions are also characterized by their high water content, generally comprised between 60% and 70% by weight.

Similarly, European patent application EP-A-1031345 describes calcium polystyrene sulfonate compositions in the form of gel, characterized in that the polymer particle size is comprised between 5 and 100 µm in diameter and the feeling of grittiness in the mouth when ingesting these preparations is thus reduced. Said compositions are prepared with water, optionally with another co-solvent; a substance for adjusting viscosity, such as a thickener, a sugar or a sugar alcohol; and a gelling agent such as agar, carrageenan, locust bean gum, alginic acid, gelatin, pectin, carboxymethyl cellulose or starch, for example.

On the other hand, reference must be made to U.S. Pat. No. 4,895,723 relating to compositions for the treatment of hypercholesterolemia containing cholestyramine and aiming to solve another problem, i.e., the bad smell that is characteristic of said resin, by means of treatment using cholestyramine with a wetting agent, which can be a soluble carbohydrate or a polyol, at a wetting agent: cholestyramine ratio comprised between 0.2:1 and 4.5:1 (corresponding to a proportion of between 16.7% and 81.8% by weight of the wetting agent with respect to the total weight of wetting agent and resin), until forming a deodorized powdery solid.

On the other hand, patent application GB-A-2404146 approaches the problems of poor palatability of medicaments with active ingredients that must be administered in high doses and proposes formulations with a creamy texture that can be taken, for example, as a spread on toast or cookies. It particularly describes a formulation with VML252, which is an ion exchange resin for the treatment of hyperphosphatemia, based on the combination of a fat and sugar in powder form as the main components of the composition, the proportion of sugar being 40% by weight.

Likewise, patent application EP-A-0422290 describes compositions for improving palatability of medicaments in general intended for patients who have a particular difficulty with swallowing, although the examples do not describe compositions with active ingredients with a high dosage regimen. Said compositions have a semisolid consistency, similar to that of pudding, and comprise the combination of the active ingredient, a non-aqueous liquid, preferably an edible oil, a considerable amount of sucrose (300 g/l), and a thickening system formed by colloidal silicon dioxide, hydrogenated castor oil and aluminum stearate.

It stands out that the compositions proposed up until now in the state of the art are not entirely satisfactory for the administration of active ingredients with a high dosage regimen because they either do not completely solve the problems derived from poor palatability, or the compositions do not sufficiently adapt to patient needs, or else the compositions are based on a high proportion of water and/or sugars which is contraindicated for patients suffering from specific pathologies.

Therefore, the need persists to provide new compositions that are suitable for the administration of active ingredients with a high dosage regimen, that have a pleasant an pleasant texture and are effective in minimizing the drawbacks derived from the poor palatability of said products and thus favoring correct patient compliance with therapy, that are free of water and have a minimal sugar content in their composition.

OBJECT OF THE INVENTION

The object of the present invention is an oral pharmaceutical composition for drugs with a high dosage regimen.

Another object of the invention is a method for the preparation of said composition.

Another object of the invention is the use of said composition for the preparation of a medicament for the treatment of various pathologies.

Another object of the invention is the adduct formed between a short-chain polyol and an ion exchange resin.

Another object of the invention is a method for the preparation of said adduct.

Another object of the invention is the use of said adduct to improve ion exchange resin palatability.

DETAILED DESCRIPTION OF THE INVENTION

The object of the present invention is a pharmaceutical composition for oral administration comprising:
a) an active ingredient with a high dosage regimen selected from the group consisting of an ion exchange resin for therapeutic use and a bulk-forming laxative,
b) an oily component selected from the group consisting of a vegetable oil, a medium-chain triglyceride, and mixtures thereof; and
c) a texturizing agent selected from the group consisting of a hydrogenated vegetable oil, a macrogolglyceride of fatty acids, and mixtures thereof,
wherein the composition is semisolid and substantially free of water and sucrose.

The authors of the present invention have developed a composition consisting of an oily continuous phase, texturized by a fatty agent, which is substantially free of water and sucrose, and having a semisolid texture, which is suitable for ingesting large amounts of active ingredients required to exert a therapeutic action, the problems of bad flavor and/or unpleasant texture being minimized.

The composition of the present invention is suitable for active ingredients with a high dosage regimen or dosage, such as ion exchange resins for therapeutic use and bulk-forming laxatives.

In the context of the invention, high dosage regimen is understood as the administration of a dose of at least 0.8 g of active ingredient per dose, preferably between 0.8 g and 5 g, and even more preferably between 0.8 g and 15 g of active ingredient per dose. The total amount to be ingested is usually more than said amount if the excipients that normally accompany the active ingredient are taken into account.

The composition of the invention has a "semisolid" consistency. In the context of the invention, said term refers to the composition having a consistency which is not rigid, but rather similar to a substantially thick and consistent, yet still malleable, paste, for example.

The composition of the invention is substantially free of water because water is not used in the preparation, but it may contain only residual moisture levels due to the components forming the composition or the environmental humidity that may be absorbed by them. The water content in the composition of the invention is generally less than 0.5% by weight, and preferably less than 0.3% by weight.

The composition of the invention is substantially free of sucrose because said sugar is not included therein, and it is therefore suitable for diabetic patients.

In the present description as well as in the claims, the singular forms of the indefinite "a", and of the definite article "the" include reference to the plural forms unless clearly indicated otherwise by the context.

Active Ingredient

In the composition of the invention, the active ingredient with a high dosage regimen is selected from the group consisting of an ion exchange resin for therapeutic use and a bulk-forming laxative.

The ion exchange resin and the bulk-forming laxative coincide in that they are drugs with a high dosage regimen because their doses are considerable, but obviously they do not belong to the same therapeutic group.

Ion Exchange Resin

Ion exchange resins are made up of a polymeric structure acting as a support for acidic or basic polar functional groups, including ions that can be exchanged with other ions present in the medium. Said resins are classified as cation or anion exchange resins, depending on the type of ions exchanged: cations ($Na^+$ or $Ca^{2+}$, for example) or anions ($Cl^-$ or $OH^-$, for example), respectively.

The therapeutic activity of these resins is based on the exchange of said ions in the gastrointestinal tract, removing or sequestering other present ions, involved in specific pathologies, and favoring fecal excretion thereof. Said resins are not absorbed as they pass through the gastrointestinal tract and are excreted without being metabolized together with the sequestered ionic substances.

In the composition of the invention, the ion exchange resin for therapeutic use is selected from the group consisting of sodium polystyrene sulfonate, calcium polystyrene sulfonate, cholestyramine, colesevelam, colestipol, and sevelamer, the characteristics of which are explained below. The ion exchange resin is preferably chosen from the group consisting of sodium polystyrene sulfonate, calcium polystyrene sulfonate and cholestyramine, and more preferably from the group consisting of sodium polystyrene sulfonate and calcium polystyrene sulfonate.

The therapeutic action of said resins generally requires taking considerably high doses comprised between 0.8 g and 15 g of resin per dose which must be taken several times a day.

Sodium polystyrene sulfonate resin (CAS registry no.: 9080-79-9, monograph no. 08668 of the Merck Index, $14^{th}$ Edition) or calcium polystyrene sulfonate resin (CAS registry no. 37286-92-3) is a vinyl benzenesulfonic acid polymer in the form of sodium or calcium salt. These are cation exchange resins indicated for the treatment of hyperkalemia, acting at the bowel level, exchanging their sodium or calcium ions for potassium ions.

In Europe, these resins are mainly sold in powder form, virtually without excipients except aromatic agents or sweeteners, which must be taken as a suspension in water. The recommended dose for these resins is usually 15 g up to 3 or 4 times a day.

Sodium or calcium polystyrene sulfonate resins are prepared according to methods that are well known for the person skilled in the art and are also available on the market under the brand name Amberlite® (Carlo Erba), for example.

Cholestyramine resin (CAS registry no.: 11041-12-6, monograph no. 02202 of the Merck Index, 14$^{th}$ Edition) is the INN identifying the styrene and divinylbenzene copolymer, functionalized with quaternary ammonium groups, in the form of chloride salt. It is a strong, basic anion exchange resin used in medicine mainly for the treatment of hypercholesterolemia as a result of its capacity to complex bile salts in the bowel, preventing absorption and favoring fecal excretion thereof. This effect triggers a compensatory mechanism consisting of an increase in bile acid synthesis at the expense of the plasma cholesterol.

Cholestyramine is usually sold in powder form which must be taken as a suspension in water or other liquids. The usual daily dose is comprised between 12 g and 16 g, distributed into 2 or 3 doses, such that each dose is usually between 4 g and 8 g.

Cholestyramine can be prepared according to methods that are well known by the person skilled in the art, by co-polymerization of the polystyrene trimethylbenzylammonium chloride with divinylbenzene. Cholestyramine is also available on the market under the brand name Dowex® 1-X2-Cl (Dow).

Colestipol resin (CAS registry no.: 26658-42-4, monograph no. 02475 of the Merck Index, 14$^{th}$ Edition) is the INN used to designate the co-polymer of diethylenetriamine and epichlorohydrin. Its therapeutic action as an anion exchange resin is based on its chloride salt form, called colestipol hydrochloride, where about 1 of every 5 nitrogens of the amino groups is protonated, forming the corresponding salt with the chloride ions.

In the context of the present invention, the term colestipol is used to refer both to colestipol in its free base form, and to its pharmaceutically acceptable salts, and preferably to colestipol hydrochloride, which is the form that is normally used therapy.

Colestipol hydrochloride is used for the treatment of hypercholesterolemia due to its bile acid binding-capacity, according to a mechanism similar to that of cholestyramine.

The usual form of presentation of commercial forms of colestipol is powder or granules that must be taken by first making a suspension in water or other liquids, or mixed with foods. The recommended daily dose is comprised between 5 g and 30 g, which can be taken in a single dose or distributed into 2 or 3 doses every day.

Colestipol hydrochloride can be prepared, for example, as described in U.S. Pat. Nos. 3,692,895 and 3,803,237.

Colesevelam hydrochloride (CAS registry no.: 182815-44-7, monograph no. 02473 of the Merck Index, 14$^{th}$ Edition) is formed by polyallylamine, cross-linked with epichlorohydrin, and alkylated with 1-bromodecane and 6-bromohexyl trimethyl ammonium bromide.

In the context of the present invention, the term colesevelam is used to refer both to colesevelam in its free base form, and to its pharmaceutically acceptable salts, and preferably to colesevelam hydrochloride, which is the form that is normally used in therapy.

Colesevelam hydrochloride is used for the treatment of hypercholesterolemia due to its bile acid binding-capacity, according to a mechanism similar to that described for cholestyramine and colestipol.

The available dosage forms of colesevelam hydrochloride are usually in tablet form containing 625 mg of active ingredient, or in powder form or granules for suspension in water, available in unit doses of 1.875 g or 3.75 g. The recommended daily dose is around 3.75 g which can be taken in a single dose, or distributed into two doses. Therefore, the amount of active ingredient to be ingested per dose is comprised between 1.875 g and 3.75 g.

Colesevelam hydrochloride can be prepared, for example, as described in the international patent application WO-A-95/34585. Furthermore, colesevelam hydrochloride is also available on the market.

Sevelamer resin (CAS registry no.: 52757-95-6; monograph no. 08474 of the Merck Index, 14$^{th}$ Edition) is the INN corresponding to the allylamine polymer cross-linked with epichlorohydrin. Around 40% of the amines are protonated, such that sevelamer is usually in the form of a salt.

In the context of the present invention, the term sevelamer is used to refer both to sevelamer resin in the free base form, and to its pharmaceutically acceptable salts, preferably to sevelamer hydrochloride or sevelamer carbonate.

Sevelamer resin, which is usually in the form of its carbonate or hydrochloride salt, is used in therapy for the treatment of hyperphosphatemia in adults subjected to dialysis due to its capacity to bind to phosphate ions in the gastrointestinal tract, preventing absorption and thus contributing to reducing blood phosphate levels.

The usual recommended dose of sevelamer is comprised between 0.8 g and 1.6 grams, which must be taken three times a day.

Sevelamer can be prepared, for example, as described in international patent application WO-A-95/05184. Furthermore, it can also be obtained on the market.

Bulk-Forming Laxative

The bulk-forming laxative included in the composition of the invention belongs to a group of substances that are not digested or are only partially digested and have a high affinity for water, such that the mechanism of action is based on the absorption of liquid in the bowel, leading to increased fecal bulk and stimulation of the peristaltic movements.

In the composition of the invention, the bulk-forming laxative is preferably selected from the group consisting of *Plantago ovata* seeds, methyl cellulose, sodium carboxymethyl cellulose, and polycarbophil or a salt thereof; and more preferably from the group consisting of *Plantago ovata* seeds and methyl cellulose.

Seeds of the *Plantago ovata* plant include a shell used as a bulk-forming laxative because it contains a high proportion of mucilage, a hygroscopic fiber having a high liquid retention capacity. Said fiber increases fecal mass bulk and provides it with consistency that is suitable for regulating intestinal transit, and it is responsible for the laxative properties of this product. The seeds of the *Plantago ovata* plant are also known as *psyllium* or *ispaghula*.

This medicament can be found on the market in the form of granules to be administered after being dispersed in water. The recommended daily dose is usually comprised between 10 g and 30 g a day, distributed into several doses, which means that the amount to be ingested is comprised between 3.5 g and 10 g per dose.

Methyl cellulose, or methyl ether cellulose (CAS registry no.: 9004-67-5, monograph no. 06040 of the Merck Index, 14$^{th}$ Edition), is a cellulose derivative that has been partially etherified with methyl groups. It can be obtained, for example, from cellulose fibers treated with methyl chloride, in basic solution with heat, as is known by the person skilled in the art.

Methyl cellulose is another laxative that also acts by increasing fecal bulk through water absorption.

Methyl cellulose can also be obtained on the market under the brand name Methocel® (Dow), Metolose® (Shin Etsu Chemical), or Benecel® (Ashland), for example.

As a rough guideline, a possible dosage regimen for methyl cellulose can be comprised between 3 g and 6 g a day, distributed into two doses, such that a usual dose of this product is comprised between 1.5 g and 3 g. This medicament can usually be found on the market in tablet form or in powder form.

Sodium carboxymethyl cellulose (CAS registry no.: 9004-32-4, monograph no. 01829 of the Merck Index, 14$^{th}$ Edition) is a cellulose derivative that has been partially etherified with sodium monochloroacetate. It is a water-absorbing compound used as a laxative because it increases fecal bulk.

Sodium carboxymethyl cellulose is available on the market under the brand name Blanose® (Ashland), for example.

As a rough guideline, a possible dosage regimen for sodium carboxymethyl cellulose can be comprised between 3 g and 6 g a day, distributed into two doses, such that a usual dose of this product is comprised between 1.5 g and 3 g.

Polycarbophil (CAS registry no.: 126040-58-2, monograph no. 01697 of the Merck Index, 14$^{th}$ Edition) is a polyacrylic acid cross-linked with divinyl glycol, which can also be administered in the form of one of its salts such as the calcium salt, for example.

Polycarbophil is available on the market under the brand name Noveon® (Lubrizol), for example.

As a rough guideline, a possible dosage regimen for polycarbophil can be comprised between 1 g and 6 g a day, distributed into two doses, such that a usual dose of this product is comprised between 0.5 g and 1 g.

The composition of the invention preferably comprises an amount of active ingredient comprised between 10% and 70% expressed by weight and more preferably between 15% and 65% expressed by weight with respect to the total weight of the composition.

For compositions comprising an ion exchange resin, the amount of active ingredient is preferably comprised between 25% and 65% by weight and more preferably between 45% and 60% by weight. For compositions the active ingredient of which is a bulk-forming laxative, the amount of the active ingredient is preferably comprised between 15% and 45% by weight and more preferably between 20% and 40% by weight, wherein all the percentages are expressed by weight with respect to the total weight of the composition.

Said compositions are preferably in unit dosage forms, containing a therapeutically effective amount of the active ingredient.

The expression "therapeutically effective amount" refers to the amount of active ingredient that must be taken in each dose to achieve the desired therapeutic effect. Said amount will be chosen depending on each active ingredient in particular and on its recommended dosage regimen well known for the person skilled in the art.

Some unit dosage forms suitable for the composition of the present invention are, for example, single-dose mini-containers or tubes. Thus, for example, when the medicament is presented in the form of a single-dose mini-container, it can advantageously be taken with the aid of a spoon.

Oily Component

The oily component of the composition of the present invention is chosen from the group consisting of a vegetable oil, a medium-chain triglyceride, and mixtures thereof.

The vegetable oil is an edible vegetable oil and can be chosen, for example, from olive oil, sunflower oil, soybean oil, rapeseed oil, peanut oil, corn oil, castor oil, cottonseed oil, sesame seed oil, wheat germ oil, grapeseed oil, and mixtures thereof. As is well known by the person skilled in the art, triglycerides from unsaturated fatty acids are the main component of said oils, and they are liquid at room temperature. The vegetable oil is preferably selected from the group consisting of olive oil, sunflower oil, soybean oil, peanut oil, and it is more preferably olive oil.

Medium-chain triglycerides are well known by the person skilled in pharmaceutical technology and are described, for example, in the book by R. C. Rowe et al., Handbook of Pharmaceutical Excipients, 4$^{th}$ edition, Pharmaceutical Press, London, 2003 [ISBN: 0-85369-472-9]. It is a mixture of triglycerides from saturated fatty acids, mainly caprylic and capric acid, which is liquid at room temperature and solidifies at a temperature of about 0° C.

The oily component is preferably selected from the group consisting of olive oil, sunflower oil, soybean oil, peanut oil, a medium-chain triglyceride, and mixtures thereof, and more preferably from the group consisting of olive oil, a medium-chain triglyceride, and mixtures thereof.

The composition of the invention has an oily component content preferably comprised between 10% and 80% by weight. For the compositions the active ingredient of which is an ion exchange resin, the amount of the oily component is preferably comprised between 10% and 50% by weight and more preferably between 15% and 45% by weight. For the compositions the active ingredient of which is a bulk-forming laxative, the amount of the oily component is preferably comprised between 40% and 80% by weight and more preferably between 50% and 75% by weight, wherein all the percentages are expressed by weight with respect to the total weight of the composition.

Texturizing Agent

In the composition of the invention, the texturizing agent is chosen from the group consisting of a hydrogenated vegetable oil, a macrogolglyceride of fatty acids, and mixtures thereof.

The texturizing agent is preferably a fatty compound that has a melting point comprised between about 30° C. and 70° C. and contributes to provide the semisolid texture to the composition of the invention.

As is well known by the person skilled in the art, hydrogenated vegetable oils are the result of the hydrogenation of vegetable oils, usually rich in unsaturated fatty acids, increasing the proportion of saturated fatty acids, which involves an increase in the melting point such that they are solid at room temperature.

Hydrogenated vegetable oils suitable for being used in the scope of the present invention are, for example, hydrogenated soybean oil, hydrogenated coconut oil, hydrogenated rapeseed oil, hydrogenated castor oil, hydrogenated cottonseed oil, or mixtures thereof. The hydrogenated vegetable oil is preferably selected from the group consisting of hydrogenated soybean oil, hydrogenated coconut oil and hydrogenated rapeseed oil, and it is more preferably hydrogenated soybean oil.

The macrogolglyceride of fatty acid is a mixture of polyethylene glycol (PEG) mono- or di-esters and glycerol mono-, di- or tri-esters with a saturated fatty acid, preferably with lauric, palmitic or stearic acid, having a residual PEG and glycerol content. Such compound is characterized by having a melting point comprised between 35° C. and 55° C. and is available on the market under the brand name Gelucire® (Gattefossé), for example. For example, Gelucire® 44/14 is lauroyl macrogol-32 glyceride, and Gelucire® 50/13 is stearoyl macrogol-32 glyceride.

In a preferred embodiment, the macrogolglyceride of fatty acid is selected from the group consisting of lauroyl macrogolglyceride and stearoyl macrogolglyceride.

In a particularly preferred embodiment, the texturizing agent is chosen from the group consisting of lauroyl macrogolglyceride, stearoyl macrogolglyceride, hydrogenated soybean oil, hydrogenated coconut oil, hydrogenated rapeseed oil, and mixtures thereof.

The composition of the invention has a texturizing agent content preferably comprised between 1% and 25%, more preferably comprised between 2% and 10%, where the percentages are expressed by weight.

Other Optional Components

Optionally, the composition of the invention further comprises one or more additional components selected from the group consisting of a polyol, a palatability-enhancing agent, a sweetener, a flavoring, an antioxidant, and mixtures thereof.

Polyol

In a preferred embodiment, the composition of the invention contains a polyol, and said polyol is preferably selected from the group consisting of glycerol, propylene glycol and mixtures thereof. The polyol is generally in an amount comprised between 2% and 50% by weight, and more preferably comprised between 3% and 37% by weight, where the percentages are expressed by weight with respect to the total weight of the composition.

When the active ingredient is an ion exchange resin, the polyol can be in the form of an adduct with the resin. In this case, the polyol content in the form of an adduct is preferably comprised between 2% and 10%, and more preferably comprised between 3% and 7%, where the percentages are expressed by weight with respect to the total of the composition. The resin composition can also contain polyol that is not in the form of an adduct but which acts like a coadjuvant of the oily component. In this case, as an coadjuvant of the oily component, the polyol is preferably in an amount comprised between 5% and 40%, more preferably comprised between 10% and 30%, where the percentages are expressed by weight with respect to the total of the composition.

The adduct formed between the polyol and the ion exchange resin is the result of an intimate mixture of the resin and the polyol, which is prepared before incorporating the active ingredient in the composition. The amount of polyol present in said adduct is preferably comprised between 5% and 25% expressed by weight with respect to the weight of the resin-polyol adduct.

All the particular embodiments, definitions and features described throughout this description for the composition comprising said ion exchange resin without forming an adduct are valid for this case, where the ion exchange resin is in the form of a resin-polyol adduct.

Therefore in a preferred embodiment of the invention, the active ingredient is an ion exchange resin selected from the group consisting of sodium polystyrene sulfonate, calcium polystyrene sulfonate, cholestyramine, colestipol, colesevelam and sevelamer, and the resin is in the form of an adduct with a polyol selected from the group consisting of glycerol, propylene glycol, and mixtures thereof. In an even more preferred embodiment, the resin is chosen from sodium polystyrene sulfonate, calcium polystyrene sulfonate and cholestyramine, and even more preferably, the resin is sodium polystyrene sulfonate or calcium polystyrene sulfonate.

In a particularly preferred embodiment, the composition with a resin-polyol adduct comprises:

between 10% and 70% by weight of active ingredient;

between 10% and 80% by weight of oily component, selected from the group consisting of olive oil, sunflower oil, soybean oil, peanut oil, a medium-chain triglyceride, and mixtures thereof; and more preferably selected from olive oil, medium-chain triglycerides, and mixtures thereof;

between 1% and 25% by weight of texturizing agent, selected from the group consisting of lauroyl macrogolglyceride, stearoyl macrogolglyceride, hydrogenated soybean oil, hydrogenated coconut oil, hydrogenated rapeseed oil, and mixtures thereof; and more preferably selected from the group consisting of lauroyl macrogolglyceride, stearoyl macrogolglyceride, hydrogenated soybean oil, and mixtures thereof, wherein the percentages are expressed by weight with respect to the total weight of the composition.

The authors of the present invention have observed that said resin-polyol adduct contributes in a surprisingly effective manner to improving palatability of the active ingredient and, therefore, of the composition as well.

Example 1 shows the result of a study in which the feeling of adherence to the buccal-esophageal mucosae of resins in the form of an adduct with respect to untreated resin was evaluated, considerable improvement being observed with the use of said adduct.

Said Example 1 also describes the preparation of a similar adduct, but using olive oil instead of a polyol. In this case, no improvement in resin palatability was detected. It was thus found that the palatability-enhancing effect of the adduct does not derive from the simple effect of solvation or coating the resin, but that the short-chain polyol provides it with a singular surprising improvement as regards how easy it is to ingest.

Therefore, another object of the invention is an adduct formed between:

(a) an ion exchange resin for therapeutic use selected from the group consisting of sodium polystyrene sulfonate, calcium polystyrene sulfonate, cholestyramine, colestipol, colesevelam and sevelamer; and (b) a polyol selected from the group consisting of glycerol, propylene glycol, and mixtures thereof, on the proviso that:

the glycerol content is less than 20% by weight, because patent application EP-A-0171528 describes pharmaceutical compositions comprising a resin with a drug absorbed thereon, in which the resin is impregnated with an amount of glycerol comprised between 20% and 30% by weight with respect to the total weight of glycerol and resin, and coated with a polymer controlling drug release, and when the resin is cholestyramine, the polyol content is less than 16.7%, where the percentages are expressed by weight with respect to the total weight of the resin-polyol adduct because U.S. Pat. No. 4,895,723 describes a cholestyramine composition in the form of a deodorized powdery solid in which the resin is treated with a polyol such as glycerol or propylene glycol to control the bad small that is characteristic of said resin. The polyol to resin ratio is comprised between 0.2:1 and 4.5:1, corresponding to between 16.7% and 81.8% by weight of polyol with respect to the total weight of polyol and resin.

The proportion of polyol in the adduct is preferably comprised between 4% and 19% by weight, and more preferably comprised between 5% and 13% by weight, wherein the percentages are expressed by weight with respect to the total weight of the resin-polyol adduct. In a particularly preferred embodiment, the polyol is glycerol.

Another object of the invention is a method for the preparation of said adduct comprising the following steps:
(i) mixing the resin and the polyol under constant stirring at a temperature comprised between 20° C. and 30° C.; and
(ii) drying the previous mixture at a temperature comprised between 40° C. and 60° C. for a period of not less than 8 hours.

The product obtained after step (i) is preferably sieved through a mesh with a mesh opening comprised between 500 microns and 700 microns.

The drying time of step (ii) is preferably not less than 12 hours and more preferably not less than 16 hours.

The drying temperature of step (ii) is preferably comprised between 40° C. and 45° C.

The product obtained after step (ii) is preferably sieved through a mesh with a mesh opening comprised between 250 microns and 350 microns.

An adduct in powder form is obtained after this process. Said adduct can be used for the preparation of a semisolid composition according to the present invention.

Another object of the invention is the use of an adduct formed between:
(a) an ion exchange resin for therapeutic use selected from the group consisting of sodium polystyrene sulfonate, calcium polystyrene sulfonate, cholestyramine, colestipol, colesevelam and sevelamer; and
(b) a polyol selected from the group consisting of glycerol, propylene glycol, and mixtures thereof,
to improve resin palatability.

Palatability-Enhancing Agent

In a preferred embodiment, the composition of the invention contains a palatability-enhancing agent. Said agent is preferably selected from the group consisting of mannitol, maltitol, xylitol, and mixtures thereof. Said substances are sugar alcohols which, in addition to their properties as natural sweeteners, also have a certain capacity to texturize the composition, to conceal bad flavors, and to provide a good feeling on the palate. The palatability-enhancing agent is preferably mannitol.

When the composition contains a palatability-enhancing agent, said agent is generally added in an amount comprised between 2% and 10% by weight, more preferably comprised between 3% and 7% by weight with respect to the total weight of the composition.

Sweetener

In a preferred embodiment, the composition of the invention contains a sweetener. Said substances provide a sweet flavor to the composition with a relatively small amount of product and without adding extra calories.

Any pharmaceutically acceptable sweetening substance can be used as is well known by the person skilled in the art such as, for example, saccharine, neohesperidin dihydrochalcone (neo-DHC), sucralose, cyclamic acid, aspartame, acesulfame potassium, stevioside, thaumatin, or mixtures thereof.

When the composition contains a sweetener, said sweetener is generally added in an amount comprised between 0.01% and 1% by weight with respect to the total weight of the composition.

Flavoring

The composition of the invention has a semisolid consistency that is pleasing to the palate and can resemble, for example, the consistency of certain food products, such as yogurt, milk cream or cream. To enhance said feeling and improve the palatability of said compositions, a flavoring substance that can be chosen from different essences for food use such as, for example, essence of mint, butterscotch, vanilla, caramel, hazelnut, nougat candy, custard, cookie, whipped milk, banana, orange oil essence, or mixtures thereof, is added in a preferred embodiment.

When the composition contains a flavoring, said flavoring is generally added in an amount comprised between 0.01% and 1% by weight with respect to the total weight of the composition.

Antioxidant

In a preferred embodiment, the composition contains an antioxidant to favor the stability of the compositions, particularly to prevent the oxidative degradation and subsequent rancidification of the unsaturated oils present in the composition.

The antioxidants suitable for being used in the compositions of the invention are, for example, propyl gallate, butylhydroxytoluene, butylhydroxyanisole, 3,3'-thiodipropionic acid, or ascorbyl palmitate, or mixtures thereof.

When the composition contains an antioxidant, said antioxidant is generally added in an amount comprised between 0.0002% and 0.5% by weight with respect to the total weight of the composition.

Preparation of the Composition

Another object of the present invention is a method for the preparation of the composition of the invention comprising the following steps:
(i) preparing a homogenous mixture comprising the oily component and the texturizing agent,
(ii) heating the mixture of step (i) at a temperature comprised between 40-100° C., and
(iii) gradually incorporating the active ingredient to the mixture of the previous step.

In step (i) the oily component is heated up to the specific temperature, and the texturizing agent can be added in solid form such that it melts upon contact with the hot liquid, all being homogenized under stirring. Alternatively, the texturizing agent can be previously melted by heating it to a sufficient temperature greater than its melting temperature and being incorporated in a melted state in the hot oily component.

The mixture of step (i) is heated at a temperature comprised between 20° C. and 100° C., more preferably at a temperature between 30° C. and 90° C., and even more preferably between 40° C. and 80° C.

The active ingredient is incorporated to said mixture when the mixture is at the desired temperature. During the addition, and as the mixture takes on consistency due to the gradual incorporation of the active ingredient, the cooling process begins by means of an external cooling system.

The process ends when the product cools to a temperature comprised between 0° C. and 30° C., whereby the composition acquires the desired consistency.

In the mixture of step (i), the polyol acting like a coadjuvant of the phase oily can also optionally be incorporated.

Other optional components such as palatability-enhancing agents, sweeteners, and antioxidants can be added to the composition either in step (i), either before or after incorporating the active ingredient, once the cooling temperature of the composition has stabilized. Aromatic agents are preferably added once the composition has been cooled.

The composition of the invention has good organoleptic properties, being pleasing to the palate and thus facilitating the ingestion of high doses of active ingredients, resulting in an improvement in therapeutic compliance with the corresponding pharmacological treatments.

Therefore, another object of the present invention is the use of the composition of the invention, the active ingredient with a high dosage regimen being an ion exchange resin, for the preparation of a medicament for the treatment of a pathology selected from the group consisting of hyperkalemia, hypercholesterolemia and hyperphosphatemia.

Another object of the present invention is the use of the composition of the invention, the active ingredient with a high dosage regimen being a laxative, for the preparation of a medicament for the treatment of constipation.

Stated otherwise, another object of the invention is the composition of the invention for use in the treatment of a pathology that can be treated with the active ingredient with a high dosage regimen selected from the group consisting of hyperkalemia, hypercholesterolemia, hyperphosphatemia and constipation, depending on the active ingredient of the composition.

Therefore, when the active ingredient is sodium polystyrene sulfonate or calcium polystyrene sulfonate, an object of the invention is the composition of the invention for use in the treatment of the hyperkalemia.

When the active ingredient is cholestyramine, colestipol or colesevelam, an object of the invention is the composition of the invention for use in the treatment of hypercholesterolemia.

When the active ingredient is sevelamer, an object of the invention is the composition of the invention for use in the treatment of hyperphosphatemia.

When the active ingredient is a bulk-forming laxative, an object of the invention is the composition of the invention for use in the treatment of constipation.

Several examples are included below to illustrate the present invention.

Example 1: Preparation of an Adduct Between a Polyol and an Ion Exchange Resin A series of resin-polyol adducts was prepared and the improvement of palatability of the adduct with respect to the untreated resin was evaluated by means of a test performed with volunteers in which the feeling of adherence to the buccal-esophageal mucosae was assessed.

Table 1 summarizes the results obtained for each of the tested adducts.

TABLE 1

| | % resin | | % polyol | | Feeling of |
|---|---|---|---|---|---|
| Adduct | Ca-PSS[1] | cholestyramine | glycerol | PG[2] | adherence |
| Compar. example | 100 | — | — | — | 3 |
| 1.1 | 78.5 | — | — | 21.5 | 1 |
| 1.2 | 88.2 | — | — | 11.8 | 2 |
| 1.3 | 82.4 | — | 17.6 | — | 1 |
| 1.4 | 88.2 | — | 11.8 | — | 1 |
| 1.5 | 90.9 | — | 9.1 | — | 2 |
| 1.6 | 93.7 | — | 6.2 | — | 2 |
| 1.7 | — | 80 | — | 20 | 1 |
| 1.8 | — | 88.9 | — | 11.1 | 2 |

[1]calcium polystyrene sulfonate
[2]propylene glycol

In all cases, the adduct was prepared by adding the polyol to the resin in a granulator at a temperature comprised between 20° C. and 30° C. and under constant stirring. It was then sieved through 600 microns and dried for about 16 hours at a temperature between 40° C. and 45° C. It was finally sieved through 300 microns, the adduct being obtained in powder form.

The feeling of adherence to mucosae was evaluated for each case with a group of 4 volunteers, and the average value was calculated. A scale of 1 to 3 was used according to the following criteria:
(1) almost imperceptible adherence
(2) substantially lower adherence with respect to the untreated resin
(3) adherence corresponding to the untreated resin A considerable improvement of palatability of the adduct with respect to the untreated resin was observed in all cases.

Following the same method described above, an adduct of calcium polystyrene sulfonate with virgin olive oil instead of with the polyol was prepared using an amount of oil equivalent to 25% by weight with respect to the total weight of the adduct. It was found, however, that said adduct did not have a palatability-enhancing effect because the sensory test with 4 volunteers resulted in a level (3) feeling of adherence, i.e., the same as the untreated resin.

Example 2: Compositions with Ion Exchange Resins and Medium-Chain Triglycerides as the Oily Component Fifteen compositions were prepared as detailed in Table 2:

TABLE 2

| | Components (g) | | | | | |
|---|---|---|---|---|---|---|
| | Active | Oily | Texturizing agent | | Polyol | |
| Composition | ingredient Ca-PSS[1] | comp. MCT[2] | Gelucire® 44/14[3] | Gelucire® 50/13[4] | glycerol | PG[5] |
| 2.1 | 15.0 | 15.0 | | 15.0 | 15.0 | |
| 2.2 | 15.0 | 15.0 | | 10.0 | 15.0 | |
| 2.3 | 15.0 | 15.0 | 10.0 | | 15.0 | |
| 2.4 | 15.0 | 15.0 | | 30.0 | | |
| 2.5 | 15.0 | 15.0 | | 10.0 | | |
| 2.6 | 15.0 | 15.0 | 5.0 | | 15.0 | |
| 2.7 | 15.0 | 15.0 | 3.0 | | | |
| 2.8 | 15.0 | 5.0 | 2.0 | | 15.0 | |
| 2.9 | 15.0 | 15.0 | 3.0 | | 3.0 | |
| 2.10 | 15.0 | 15.0 | 1.0 | | | |
| 2.11 | 15.0 | 15.0 | 2.0 | | | |
| 2.12 | 15.0 | 10.0 | 3.0 | | 10.0 | |
| 2.13 | 15.0 | 10.0 | 6.0 | | 10.0 | |
| 2.14 | 15.0 | 5.0 | 2.0 | | 10.0 | |
| 2.15 | 15.0 | 8.1 | 5.0 | | 3.2 | 4.1 |

[1]calcium polystyrene sulfonate
[2]medium-chain triglycerides
[3]lauroyl macrogolglycerides
[4]stearoyl macrogolglycerides
[5]propylene glycol These compositions were prepared by heating the oily component together with the polyol(s) to a temperature of about 60° C., the texturizing agent then being added. Once it is melted, calcium polystyrene sulfonate is added little by little under stirring, while at the same time this mixture gradually cooled off to about 25° C., at which time the product acquired the suitable semisolid consistency.

The obtained composition was packaged in single-dose containers in the form of heat-sealed leak-tight mini-containers made of aluminum foil with a lid made of the same material and with a suitable capacity. Each mini-container contained 15 g of calcium polystyrene sulfonate, corresponding to the usual recommended dose.

Example 3: Compositions with Ion Exchange Resins and Olive Oil as the Oily Component Five compositions were prepared using the ingredients detailed in Table 3:

TABLE 3

| Function | Component | 3.1 | 3.2 | 3.3 | 3.4 | 3.5 |
|---|---|---|---|---|---|---|
| | | | | Amount (g) | | |
| Active ingredient | Ca-PSS[1] cholestyramine | 15 | 15 | 4 | 15 | 15 |
| Texturizing agent | Gelucire ® 44/14[2] hydrogenated soybean oil | 2 | 2 | 1 | 1 | 2 |
| Oily comp. | olive oil | 4.8 | 12 | 4 | 11 | 12 |
| Polyol | glycerol PG[3] | 3.2 4.10 | | | 1 | 2 |
| Palatability-enhancing agent | mannitol | 2 | 2 | | | |
| Sweetener | saccharine | 0.02 | 0.02 | | | |
| | sucralose | | | 0.028 | 0.027 | 0.027 |
| | neo-DHC | | | 0.016 | 0.016 | 0.016 |
| Aromatic agent | nougat candy aroma | 0.01 | 0.01 | | | |
| | vanilla aroma | | | | 0.048 | 0.048 |
| | hazelnut aroma | | | | 0.032 | 0.032 |
| | orange essence | | | 0.017 | | |

[1]calcium polystyrene sulfonate
[2]lauroyl macrogolglycerides
[3]propylene glycol Compositions 3.1, 3.2 and 3.3 were prepared by heating the olive oil (together with the mannitol and/or polyols, according to each case) to a temperature of about 60° C. Gelucire® 44/14, previously melted at a temperature between 50° C. and 70° C., was incorporated in said mixture.

The resin was then slowly added to the molten mixture under constant stirring while at the same time this mixture cooled off to a temperature of about 20° C. The sweetener and the aromatic agent were finally incorporated, also under stirring.

A resin and polyol (glycerol in this case) adduct was previously prepared in compositions 3.4 and 3.5. To that end, the polyol was added to the resin in a granulator under constant stirring at a temperature comprised between 20° C. and 30° C. It was then sieved through 600 microns and dried for 16 hours at a temperature comprised between 40° C. and 45° C. It was then sieved through a mesh with a mesh opening of 300 microns, the adduct being obtained in powder form and subsequently incorporated to the composition. The composition was prepared similarly to that described above, by means of incorporating the texturizing agent to the olive oil, which is previously heated at a temperature of between 50° C. and 70° C., under stirring until the texturizing agent melts completely. The adduct was then immediately added little by little, and as it was added this mixture cooled off to a temperature of about 17° C. Sweeteners and aromatic agents were then added and it was homogenized until obtaining the final product.

Like in the preceding example, the compositions were packaged in single-dose mini-containers.

Example 4: Compositions with Laxatives

Seven compositions were prepared with *Plantago ovata* and methyl cellulose as laxative active ingredients as detailed in Table 4.

TABLE 4

| Function | Component | 4.1 | 4.2 | 4.3 | 4.4 | 4.5 | 4.6 | 4.7 |
|---|---|---|---|---|---|---|---|---|
| | | | | Amount (g) | | | | |
| Active ingredient | *Plantago ovata* | 3.5 | 3.5 | — | — | — | — | — |
| | methyl cellulose | — | — | 1.0 | 1.0 | 1.0 | 1.0 | 1.0 |
| Texturizing agent | hydrogenated soybean oil | 1.4 | 1.0 | 0.3 | 0.6 | 0.4 | 0.2 | 0.1 |
| Oily comp. | olive oil | 10.5 | 7.5 | 2.0 | 3.0 | 3.0 | 3.0 | 3.0 |
| Sweetener | neo-DHC | 0.007 | 0.004 | — | — | 0.002 | 0.002 | 0.002 |
| | sucralose | 0.014 | 0.008 | — | — | 0.003 | 0.004 | 0.004 |
| Aromatic agent | lemon aroma | — | — | — | — | 0.010 | 0.020 | 0.020 |
| | orange essence | 0.020 | 0.020 | — | — | — | — | — |

Compositions 4.1 to 4.7 were prepared according to a method similar to that of Example 2, in which the olive oil was heated together with the hydrogenated soybean oil at a temperature of about 60° C., and the laxative active ingredient was then incorporated under continuous stirring. This mixture cooled off to room temperature as the addition was performed, optionally, the sweeteners and aromatic agents finally being incorporated under continuous stirring until a homogenous mass was obtained.

The obtained compositions were also packaged in single-dose containers.

The invention claimed is:
1. A pharmaceutical composition for oral administration consisting of:
   a) an active ingredient with a high dosage regimen selected from the group consisting of an ion exchange resin for therapeutic use and a bulk-forming laxative,
   b) an oily component selected from the group consisting of a vegetable oil, a medium-chain triglyceride, and mixtures thereof,
   c) a texturizing agent selected from the group consisting of a hydrogenated vegetable oil, a macrogolglyceride of fatty acids, and mixtures thereof,
   d) a sweetener selected from the group consisting of saccharine, neohesperidin dihydrochalcone (neo-

DHC), sucralose, cyclamic acid, aspartame, acesulfame potassium, stevioside, thaumatin, and mixtures thereof, wherein said sweetener is 0.01% to 1% of the total weight of the composition,
e) a palatability-enhancing agent, wherein said palatability-enhancing agent is 2%-10% of the total weight of the composition and
f) optionally one or more additional components selected from the group consisting of a polyol, a palatability enhancing agent, a sweetener, a flavoring, an antioxidant, and mixtures thereof;
wherein the composition is semisolid and substantially free of water and sucrose, and wherein a high dosage regimen corresponds to the administration of a dose of at least 0.8 g of active ingredient.

2. The composition according to claim 1, wherein the active ingredient is an ion exchange resin selected from the group consisting of sodium polystyrene sulfonate, calcium polystyrene sulfonate, cholestyramine, colesevelam, colestipol and sevelamer.

3. The composition according to claim 2, wherein the active ingredient is an ion exchange resin selected from the group consisting of sodium polystyrene sulfonate, calcium polystyrene sulfonate and cholestyramine.

4. The composition according to claim 1, wherein the active ingredient is a bulk-forming laxative selected from the group consisting of *Plantago ovata* seeds, methyl cellulose, sodium carboxymethyl cellulose, and polycarbophil or a salt thereof.

5. The composition according to claim 4, wherein the bulk-forming laxative is selected from the group consisting of *Plantago ovata* seeds and methyl cellulose.

6. The composition according to claim 1, wherein the amount of active ingredient ranges from 10% to 70% expressed by weight with respect to the total weight of the composition.

7. The composition according to claim 1, wherein the oily component is selected from the group consisting of olive oil, sunflower oil, soybean oil, peanut oil and a medium-chain triglyceride.

8. The composition according to claim 1, wherein the content of the oily component ranges from 10% to 80% expressed by weight with respect to the total weight of the composition.

9. The composition according to claim 1, wherein the texturizing agent is chosen from the group consisting of lauroyl macrogolglyceride, stearoyl macrogolglyceride, hydrogenated soybean oil, hydrogenated coconut oil, hydrogenated rapeseed oil, and mixtures thereof.

10. The composition according to claim 1, wherein the texturizing agent is in an amount ranging from 1% to 25%.

11. The composition according to claim 1, wherein the polyol is selected from the group consisting of glycerol, propylene glycol and mixtures thereof.

12. The composition according to claim 11, wherein the polyol is in an amount ranging from 2% to 50% expressed by weight with respect to the total weight of the composition.

13. The composition according to claim 2, wherein the ion exchange resin is in the form of an adduct with a polyol selected from glycerol, propylene glycol, and mixtures thereof, wherein the adduct formed between the polyol and the ion exchange resin is the result of an intimate mixture of the resin and the polyol.

14. The composition according to claim 13, wherein the amount of polyol in the adduct ranges from 5% to 25% expressed by weight with respect to the weight of the resin-polyol adduct.

15. The composition according to claim 1, wherein the active ingredient is in an amount ranging from 10% to 70%,
the oily component is in an amount ranging from 10% to 80%, and is selected from the group consisting of olive oil, sunflower oil, soybean oil, peanut oil, a medium-chain triglyceride, and mixtures thereof, and
the texturizing agent is in an amount ranging from 1% to 25% expressed by weight, and is selected from the group consisting of lauroyl macrogolglyceride, stearoyl macrogolglyceride, hydrogenated soybean oil, hydrogenated coconut oil, hydrogenated rapeseed oil, and mixtures thereof,
wherein the percentages are expressed by weight with respect to the total weight of the composition.

16. The composition according to claim 1, wherein the palatability-enhancing agent is selected from the group consisting of mannitol, maltitol, xylitol, and mixtures thereof.

17. A method of treating a pathology in a patient comprising administering a composition according to claim 1 to a patient in need thereof, wherein the pathology is selected from the group consisting of hyperkalemia, hypercholesterolemia and hyperphosphatemia and wherein the active ingredient with a high dosage regimen is an ion exchange resin.

* * * * *